United States Patent [19]

Foung et al.

[11] Patent Number: 4,764,465

[45] Date of Patent: Aug. 16, 1988

[54] HUMAN MONOCLONAL ANTIBODY AGAINST GROUP A RED BLOOD CELLS

[75] Inventors: Steven K. H. Foung, San Francisco; Andrew R. Raubitschek, Palo Alto; Edgar G. Engleman, Atherton; F. Carl Grumet, Stanford; James W. Larrick, Woodside, all of Calif.

[73] Assignees: Cetus Corporation; The Board of Trustees of the Leland Stanford Junior University, both of Stanford, Calif.

[21] Appl. No.: 913,638

[22] Filed: Sep. 30, 1986

Related U.S. Application Data

[63] Continuation of Ser. No. 604,069, Apr. 26, 1984, abandoned.

[51] Int. Cl.$^4$ .................... G01N 33/53; G12N 15/00
[52] U.S. Cl. .................... 435/172.2; 435/172.1; 436/548; 424/11; 935/81; 935/89; 935/93; 935/96; 935/99; 935/102; 935/103; 530/387
[58] Field of Search ................. 436/520, 548; 435/7, 435/68, 172.2, 240, 241; 935/81, 89, 96, 99, 102, 106, 110; 424/11

[56] References Cited

U.S. PATENT DOCUMENTS

| | | | |
|---|---|---|---|
| 4,451,570 | 5/1984 | Royston et al. | 435/240 |
| 4,608,337 | 8/1986 | Croce | 436/548 |
| 4,618,486 | 10/1986 | Lundblad | 436/520 |
| 4,618,577 | 10/1986 | Handley et al. | 436/548 |
| 4,634,664 | 1/1987 | Oestberg | 435/241 |
| 4,634,666 | 1/1987 | Engleman et al. | 435/5 |

FOREIGN PATENT DOCUMENTS

WO83/03477  10/1983  PCT Int'l Appl. ............. 424/11
2097425  11/1982  United Kingdom .

OTHER PUBLICATIONS

Abe et al., The Antibody Specific to Type 1 Chain Blood Group A Determinant, The Journal of Immunology, 132 (4), Apr. 1984, 1951–1954.
Voak, D. et al., Vox Sang, vol. 39, pp. 134–140, 1980.
Edelman et al., Immunology, vol. 44, No. 3, 549–554, 1981 (Abstract).
Chemical Abstracts, vol. 100, 190042u, 1984.
Chemical Abstracts, vol. 100, 101320t, 1984.

*Primary Examiner*—Sidney Marantz
*Assistant Examiner*—Janelle Graeter
*Attorney, Agent, or Firm*—Ciotti & Murashige, Irell & Manella

[57] ABSTRACT

A human monoclonal antibody that directly agglutinates type A human red blood cells is described. The exemplified antibody is an IgM and is produced by hybrid cells lines S-H22 and HHA1. The antibody is useful as an ABO typing reagent.

7 Claims, No Drawings

HUMAN MONOCLONAL ANTIBODY AGAINST GROUP A RED BLOOD CELLS

This invention was made with Government support under HL 29572 awarded by the National Institutes of Health. The Government has certain rights in this invention.

This application is a continuation of co-pending patent application Ser. No. 604,069, filed Apr. 26, 1984 now abandoned.

DESCRIPTION

TECHNICAL FIELD

This invention is in the field of biotechnology. More particularly, it is in the field of immunohematology and concerns a human anti-blood group A antibody.

BACKGROUND ART

The surfaces of red blood cells contain large numbers of antigenic determinants that are classified into blood groups. One well-known group of red blood cell surface antigens is the ABO group. These antigens are used extensively in blood typing. Most blood typing tests are based on hemagglutination and involve mixing a blood sample with a panel of typing reagents that react with various surface antigens and cause the cells to agglutinate. The presence or absence of agglutination is an indication of blood type.

ABO typing reagents have traditionally been derived from whole human blood. Non-human blood type reagents, including murine monoclonal antibodies, have been reported. Voak, D., et al, *Vox Sang* (1980) 39:134–140 describes a murine monoclonal anti-A antibody. British patent application 209,7425 (published 3 Nov. 1983) describes a murine monoclonal anti-B antibody.

DISCLOSURE OF THE INVENTION

The present invention concerns human anti-blood group A monoclonal antibody S-H22 and functional equivalents thereof.

The permanent hybrid cell lines that produce said antibody and are exemplified herein, and progeny of said lines are another aspect of this invention.

Labeled derivatives of said antibody comprising a conjugate of the antibody and a detectable label are also part of the invention.

Another aspect of this invention is a method of determining whether a human blood sample contains red cells having a type A antigenic determinant comprising incubating the sample with said monoclonal antibody or functional equivalent and observing whether the antibody or functional equivalent agglutinates the cells.

MODES FOR CARRYING OUT THE INVENTION

As used herein the term "functional equivalent" means a human monoclonal antibody that recognizes the same antigenic determinant and crossblocks the human monoclonal antibody designated S-H22 herein. It is intended to include antibodies of the same or different immunoglobulin class and antigen binding fragments (e.g., Fab, F(ab)2, Fv) of the monoclonal antibody.

As used herein the term "cell line" refers to individual cells, harvested cells, and cultures containing cells so long as they are derived from cells of the cell line referred to.

As used herein with respect to the exemplified anti-A producing hybrid cell lines the term "progeny" is intended to include all derivatives, issue, and offspring of cells of those lines regardless of generation or karyotypic identity. In this regard, it is well known that karyotypic changes may be induced or occur spontaneously depending upon the conditions under which the cells are maintained.

As used herein the terms "blood group A" and "type A" are synonymous and are intended to include all red blood cells having one or more determinants found solely on group A blood cells (i.e., all A and AB groupings).

Monoclonal antibody S-H22 was originally produced by an EBV-transformed human lymphocyte, designated E6C6. Supernatant from E6C6 was tested against random human donors+ red blood cells of groups A1, A2, B, O, Aint, A1B, and A2B. The supernatant reacted with all A groups and no others. Supernatant was also tested against a panel of rare A subgroups (A3, Ax, Aend, A5(1)) together with two commercial antisera. The table below shows the results of this testing.

| Cell | Monoclonal Antibody | Commercial* | Commercial A,B |
|---|---|---|---|
| A3 | 2 (M.F.) | 3 (M.F.) | 3 (M.F.) |
| Ax | +w | 1 | 2 |
| Aend | +w | +w | +w |
| A5(1) | 1 | 0 | 0 |

*Obtained from Dade (A-A26-16, A,B-0151-2B)
0 = no reaction;
+w = weak, but definitely positive reactivity;
1-3 = increasing strength.
M.F. = mixed field reaction of positive reactivity;

This monoclonal antibody was also tested by a commercial blood banking laboratory on previously documented red cell phenotypes of groups A2, A1, A1B, A2B, B and O. The antibody agglutinated all A and AB phenotypes but did not agglutinate the B and O phenotypes.

The class of the antibody produced by E6C6 was determined by conventional isotyping procedures to be IgM with kappa light chain.

Stable permanent cell lines producing this antibody were made by fusing E6C6 to an EBV-transformed human lymphoblastoid line (LTR228) and to a mouse x human hybrid (SBC-H20). The details of these fusions and the resulting hybrid cell lines are given in the following examples. These examples are not intended to limit the invention in any manner.

Preparation of E6C6

Lymphocytes were isolated from a spleen removed from a type O individual (who required splenectomy because of a severe hemolytic anemia) by separation on a FicollHypaque density gradient of specific gravity 1.077 according to the procedure of Boyum, A., *Scan J Lab Clin Invest* (1968) 21:77. The cells were cultured at a cell concentration of $2 \times 10^6$/ml in Iscove's medium (ICM) containing 15% heat-inactivated fetal calf serum (FCS) and 0.03% type A1 red blood cells. After three days, T cells were removed by the single step rosetting method of Saxon, A., et al *J Immunol Methods* (1976) 12:285 using 2-aminoethylesothioronium bromide hydrobromide, and the residual B cells were transformed by the EBV-containing supernatant from the marmoset line B-958 according to the procedure of Sly, W. S., et al *Tissue Antigens* (1976) 7:165. The cells from the transforming mixture were transferred to microtiter plates at a concentration of $10^5$ cells per well and cultured for 14 days in ICM containing 15% FCS.

Anti-A Ig-containing wells were identified by the type A red blood cell (ARBC) agglutination test described by Parker, J., et al, *Transfusion* (1978) 18:417. Two positive wells were identified, but only one, designated E6, survived. E6 cells were enriched by treatment with papain and rosetting with ARBC. Rosetting cells were separated by ficoll-hypaque gradient centrifugation (yield ~10%) and then cloned in soft agar. Colonies were picked, expanded and assayed for anti-A activity by ARBC agglutination. One subclone, identified as E6C6, was chosen for fusion with the fusion partners described below.

Fusion Partners

A. Ouabain-resistant LTR228

LTR228 is a subvariant of the WI-L2 line (Levy, J. A., et al, *Cancer* (1968) 22:517). It was derived from a mycoplasma-contaminated generic WI-L2 parent by cloning the parent in soft agar, decontaminating the parent line, and culturing it in Iscove's medium containing 20 μg/ml 6-thioguanine (6-TG). LTR228 was selected from among the 6-TG resistant clones on the basis of its ability to fuse efficiently with normal B lymphocytes to produce stable human x human hybridomas.

LTR228 has a hyperdiploid modal chromosome number of 8. LTR228 cells are characterized by having: extra copies of chromosome 13 and 20; a Robertsonian translocation between chromosomes 14 and 21; a copy of chromosome 8 with an enlarged short arm composed of a homogeneously staining region; and a marker 21 which has a translocation from the distal end of chromosome 11. LTR228's karyotype is: 48,XY,+13,+20,-14,+t(14q;21q),21,+der(21),t(11;21) (q13;p11),8pt+. LTR228 secretes small amounts of IgMκ and has a doubling time of about 16 hr. Its rapid growth rate and high cloning efficiency both in soft agar and by limiting dilution are important characteristics of the line.

LTR228 is the subject of a concurrently filed U.S. patent application titled "Human Lymphoblastoid Cell Line and Hybridomas Derived Therefrom."

LTR228 cells were made resistant to ouabain by culturing them in ICM containing $10^{-8}$ ouabain. Resistant cells were expanded and the concentration of ouabain was increased gradually. The procedure was repeated until the cells could survive $10^{-6}$ M ouabain. Clones were selected from soft agar supplemented, with 6-TG (20 μg/ml) and ouabain ($10^{-6}$ M).

B. SBC-H20

SBC-H20 is a hybrid of the murine myeloma line SP2/08A2 and a human peripheral B lymphocyte (PBL). SP2/08A2 was obtained for use as the immortalizing partner from Frank Fitch, University of Chicago. This cell line is freely available and can be used without restriction. PBLs were isolated from the heparinized plasma of a normal human donor by Ficoll-Hypaque gradient as described by Boyum, A., supra. The PBLs and myeloma cells were mixed at a 1:1 ratio, washed once in RPMI 1640 medium (Gibco), and pelleted at 250 ×g for 10 min. The pellet was gently resuspended in 1 ml of RPMI with 40%–45% (volume/volume) polyethylene glycol (PEG) solution, MW 1430-1570 (BDH Chemicals, Poole, England) which was pre-warmed to 37° C. After two min at room temperature, the cell suspension was diluted to 6 ml with RPMI, centrifuged at 500×g for 3 min and, beginning 8 min from the onset of fusion, the cell pellet washed with RPMI containing 10% FCS. The pelleted cells were plated in multi-well trays using suitable dilutions to obtain individual clones. The colonies were grown on AH selection medium containing 2 μg/ml azaserine and 100 μM hypoxanthine, and successful clones were assayed for immunoglobulin production and for HLA surface proteins.

A hybrid clone which had had a stable immunoglobulin production for 6 months, and which was consistently producing HLA surface protein was selected.

This clone was then placed in ICM containing 10% FCS, 2 mM glutamine, 100 units penicillin, 100 mg streptomycin per ml, as well as $2 \times 10^{-6}$ M 6-TG. The concentration of 6-TG was progressively increased to $2 \times 10^{-5}$ M over a period of approximately 30 days. The resulting mutant hybrids were sub-cloned, and the colonies tested for immunoglobulin secretion. A non-secreting subline which was HAT/AH sensitive, resistant to $10^{-6}$ M ouabain, and which retained ability to produce HLA surface antigen, was designated SBC-H20.

SBC-H20 is the subject of previously copending U.S. patent application titled "A Human-Murine Hybridoma Fusion Partner" filed 6 Jan. 1984 under Ser. No. 568,739, now U.S. Pat. No. 4,634,666, issued Jan. 6, 1987. The cell line has been deposited with the ATCC, and is identified by deposit ATCC No HB 8464.

Fusion Protocols

A. Ouabain-resistant LTR228 x E6C6

The fusion mixture contained PEG 4000, 40% (w/v); dimethylsulfoxide (DMSO), 10% (v/v) in Hank's balanced salt solution (HBSS)$-/+$($Ca^{2+}$ free, 2 mM $MgSO_4$), supplemented with 5 μg/ml poly-L-arginine (Sigma, 70K150K). Forty g of PEG 4000 were combined with 10 ml of DMSO and 50 ml of HBSS$-/+$. The mix was autoclaved for 25 min. When the solution had cooled to room temperature, poly-L-arginine from a filter sterilized 1000x stock solution was added to obtain a final concentration of 5 μg/ml. Before use, the pH of the fusion mixture was adjusted to 7.9 with sterile 0.1 N NaOH. Fresh fusion mixture was made every two to three weeks.

Plates (Costar 3506, 6-well cluster, 35 mm well diameter) were prepared as follows: 2 ml of HBSS$-/+$ and 50 μ sterilized, 100 μg/ml, peanut agglutinin (PNA, Sigma) were added to each well. Plates were incubated at 37° C. for at least one hr prior to use. PNA stock was stored frozen, and a freshly thawed aliquot was used to coat fusion cells. Smaller sized wells were used if cell numbers were limited.

Parent cells were washed twice in HBSS$-/+$ at room temperature and subsequently resuspended and combined in HBSS$-/+$ warmed to 37° C. Two ml of the suspension (10–20 million cells) were added to each pretreated well containing PNA coating solution. Plates were spun at 400–500×g, room temperature, for six min to form a monolayer of cells. Supernatant was then aspirated off the plates.

Two ml of fusion mixture warmed to 37° C were carefully added down the side of the fusion cell. After one min, the PEG solution was diluted with 37° C 5% DMSO in HBSS$-/+$(filter sterilized) at a rate of 2 ml/min (0.5 ml every 15 sec) for three min (6 ml). The fusion dilution mixture (FDM) was then added at a rate of 4 ml/min until the well was filled. FDM was always added down the side of the well, so as not to disturb the monolayer, and the plates were constantly swirled to ensure optimal mixing.

At this stage, the wells were aspirated. The remaining film of PEG mixture was diluted at a rate of 2 ml/min for two min with warm FDM. Again the plate was constantly swirled. Over a period of 15 sec, 5 ml of 37° C HBSS−/+ were added to the fusion well, and all supernatant was aspirated from the monolayer. Finally, each fusion well was washed twice with 5-10 ml of warm HBSS−/+. Five ml of warm ICM, 15% FCS, were added to each well, and the plates were incubated at 37° C. The day following fusion the cells were plated at $10^5$ cells/well in ICM containing azaserine (2 $\mu$g/ml) and ouabain ($10^{-6}$ M). Growing hybrids were visible by day 10 and growing wells were tested for anti-A activity by hemagglutination on day 21. Positive wells were recloned in soft agar. A sample of one of the anti-A producing subclones, designated HHA1, was selected for preservation and deposit.

B. SBC-H20×E6C6

This trioma was made using the above desribed fusion protocol that was used to prepare SBC-H20 except that a 1:10 cell ratio (E6C6:SBC-H20) was used (or SP2/08A2 cells as a control). After washing in RPMI with 10% FCS, the cells were plated in microtiter plates at a density of $1\times10^6$ cells per well over irradiated mouse spleen feeder cells and grown under a humidified 6% $CO_2$ atmosphere at 37° C. Two similar selection media were used: HAT selection medium containing 100 $\mu$M hypoxanthine, 800 nM aminopterin, 15 $\mu$M thymidine, as well as 0.1 mM ouabain and AH selection medium containing 2 $\mu$g/ml azaserine, 100 $\mu$M hypoxanthine and 0.1 $\mu$M ouabain. Unfused SBC-H20 and unfused E6C6 were dead after 10 days. The resulting fused cells were further selected for 10 days using 0.1 $\mu$M ouabain and for 14 days by HAT or AH. Individual clones were verified by sequential soft agar and limiting dilution cloning.

Verification of SBC-H20×E6C6 Triomas by Chromosomal Analysis

Chromosome preparations were obtained from the trioma clones and assessed to verify successful fusions. Chromosome, preparations were made as follows: approximately $10^6$ cells per ml were placed in basic growth medium containing vinblastine at 0.5 $\mu$g per ml (Lilly), incubated for 3 hr, and centrifuged at 250×g for 10 min. The cell pellet was resuspended in 5 ml of hypotonic solution (growth medium/distilled water, 1:4) for 10 min and the cells repelleted, washed twice in fixative comprising methanol:glacial acetic acid, 5:1, and finally resuspended in a few drops of fixative. The suspensions were air dried on microscope slides, stained with Giemsa (Sigma) and examined microscopically.

The triomas were thus shown to contain 100-110 chromosomes, of which 70-75 have acrocentric centromeres suggestive of murine origin, and the rest of which have metacentric centromeres, suggestive of human origin. (The parent SBC-H20 cells have 75-80 chromosomes, 3 with metracentric centromeres.)

Anti-A Antibody Production by SBC-H20×E6C6 Trioma

Supernatants of several of the triomas were tested for specific antibody production against red blood cells using an agglutination assay. A positive result was defined using V bottom microtiter trays (Falcon Lab) and assuming macroscopic agglutination according to the method of Parker, J., et al Transfusion (1978) 18:417 after addition of test solution and centrifugation at 250×g for 45 sec. Quantitation was achieved by testing serial doubling dilutions with 3% bovine serum albumin in normal saline the end point being defined as the limiting dilution. The results are shown in the table below.

|  | Number of Wells with Anti-A Activity | Titer* |
| --- | --- | --- |
| Secreting Line |  |  |
| E6C6 |  | 1:2,000 |
| SP2/08A2 × E6C6 |  |  |
| Parents | 19/22 | 1:32 |
| Clones | 0/23 | 0 |
| SBC-H20 × E6C6 |  |  |
| Parents | 29/31 | 1:8,192 |
| Clones | 13/21 | 1:16,384 |
| Subclones | 36/53 | 1:32,768 |

*Maximum dilution permitting detection of agglutination

The triomas formed by fusion with SBC-H20 were capable of secreting the monoclonal anti-A titers at least four-fold higher than E6C6 through several transfers, and for a period of more than 8 months. The amounts produced are more than 10 $\mu$g/ml; comparable to the level of production by a typical murine-murine hybridoma. The quantity produced by E6C6, however, was approximately 10-fold less. The specificity of the antibody produced by the trioma was tested using the agglutination assay against 173 donor-derived red blood cell preparations of A, AB, B and O phenotypes. The results of these tests are reported on the table below.

| Positively Testing Cells | Number Tested | % Positive |
| --- | --- | --- |
| A2 | 13 | 100 |
| A1 | 59 | 100 |
| A1B | 4 | 100 |
| A2B | 1 | 100 |
| Aint | 7 | 100 |
| B | 16 | 0 |
| O | 71 | 0 |

A sample of the trioma, designated S-H22, was selected for preservation and deposit.

The antibody may be produced by growing the exemplified hybrid cell lines in a suitable culture medium such as ICM or RPMI (preferably serum free) or in vivo in a host such as a nude mouse. If desired, the antibody may be separated from the culture medium or body fluid, as the case may be, by conventional techniques such as ammonium sulfate precipitation, ion exchange chromatography, affinity chromatography, electrophoresis, microfiltration, and ultracentrifugation.

The monoclonal antibody may be used in conventional manual or automated ABO agglutination typing tests to ascertain whether blood samples contain blood type A cells. These tests are based on the ability of the antibody to agglutinate blood type A cells selectively and involve incubating the sample in a container such as a tube or plate well with the antibody and observing the degree of agglutination either visually or spectrometrically. The rate of sedimentation may be enhanced by centrifugation, if desired. Supernatant from the cultures of the exemplified anti-A producing hybrid cells may be used directly in these tests.

Labeled derivatives of the antibody may be made for use in ABO typing via other immunoassay techniques such as radioimmunoassay, fluorescence immunoassay or enzyme immunoassay. The labels that are used in making labeled versions of the antibody include moieties that may be detected directly, such as fluorochromes and radiolabels, as well as moieties, such as enzymes, that must be reacted or derivatized to be detected. Examples of such labels are $^{32}P$, $^{125}I$, $^{3}H$, $^{14}C$, fluorescein and its derivatives, rhodamine and its derivatives, dansyl, umbelliferone, luciferia, 2,3-dihydrophthalazinediones, horseradish peroxidase, alkaline phosphates, lysozyme, and glucose-6-phosphate dehydrogenase. The antibody may be tagged with such labels by known methods. For instance, coupling agents such as aldehydes, carbodiimides, dimaleimide, imidates, succinimides, bisdiazotized benzandine and the like may be used to tag the antibodies with the above-described fluorescent, chemiluminescent, and enzyme labels.

Blood typing tests using these labeled derivatives will involve incubating a blood sample with the labeled antibody and detecting the presence or absence of labeled immune complexes on the cells in the sample via the label. The details of such procedures are well known in immunoassay art.

Samples of the hybrid cell lines HHA1 and S-H22 were deposited at the American Type Culture Collection (ATCC), 12301 Parklawn Drive, Rockville, Maryland, U.S.A. The deposit and accession numbers are listed below.

| Cell Line | Deposit Date | Accession No. |
| --- | --- | --- |
| S-H22 | 1 March 1984 | HB8518 |
| HHA1 | 28 March 1984 | HB8534 |

These deposits were made under the Budapest Treaty and will be maintained and made available in accordance with the provisions thereof.

Modifications of the above-described modes for carrying out the invention that are obvious to those of skill in the field of hybridoma technology, immunohematology, and related fields, are intended to be within the scope of the following claims.

We claim:

1. A trioma cell line capable of secreting a human monoclonal antibody specific against A red blood cell antigen, said cell line comprising
   a fusion partner produced by fusing mouse myeloma cells and non-malignant human B-lymphocytes, selecting fusion products which show stable immunoglobulin secretion and HLA surface antigen production in culture, treating the selected fusion products with a mutagen, and selecting mutagenized fusion products which retain the ability to produce HLA surface antigen, show no immunoglobulin secretion, and are unable to survive in a growth medium which allows growth of a successful fusion product formed by fusing the fusion partner with a human immunoglobulin-secreting B-lymphoid cell, and
   fused with a fusion partner, an B-lymphoid cell which is derived from a blood type O human donor, activated with Epstein-Barr virus, and selected for secretion of anti-A red blood cell antibody.

2. The cell line of claim 1, which has the characteristics of ATCC #HB 8518.

3. An anti-A red blood cell antibody secreted by the trioma cell line of claim 1.

4. The antibody of claim 3, which is secreted by the cell line having the characteristics of ATCC #HB 8518.

5. A method of producing a human monoclonal antibody which is specific against a red blood cell antigen, comprising
   providing a fusion partner produced by fusing mouse myeloma cells and non-malignant human B-lymphocytes, selecting fusion products which show stable immunoglobulin secretion and HLA surface antigen production is culture, treating the selected fusion products with a mutagen, and selecting mutagenized fusion products which retain the ability to produce HLA surface antigen, show no immunoglobulin secretion, and are unable to survive in a growth medium which allows growth of a successful fusion product formed by fusing the fusion partner with a human immunoglobulin-secreting B-lymphoid cell, and
   fusing the fusion partner with a B-lymphoid cell which is derived from a blood type O human donor, activated with Epstein-Barr virus, and selected for secretion of anti-A red blood cell antibody, and
   selecting fusion products which secrete anti-A red blood cell antibodies.

6. The method of claim 4, wherein the fusion partner has the characteristics of ATCC No HB 8464.

7. The method of claim 5, wherein the fusion product selected has the characteristics of ATC. #HB 8518.

* * * * *